United States Patent
Kobold et al.

(10) Patent No.: US 12,352,768 B2
(45) Date of Patent: Jul. 8, 2025

(54) AUTOMATIC SAMPLE WORKFLOW FOR LC-MS BASED HBA1C MEASUREMENT ON INTACT PROTEIN LEVEL

(71) Applicant: Roche Diagnostics Operations, Inc., Indianapolis, IN (US)

(72) Inventors: Uwe Kobold, Weilheim (DE); Andreas Leinenbach, Oberhausen (DE); Indranil Mitra, München Süd (DE); Holger Busskamp, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 952 days.

(21) Appl. No.: 17/370,180

(22) Filed: Jul. 8, 2021

(65) Prior Publication Data
US 2021/0333291 A1  Oct. 28, 2021

Related U.S. Application Data

(63) Continuation of application No. PCT/EP2020/051041, filed on Jan. 16, 2020.

(30) Foreign Application Priority Data

Jan. 17, 2019  (EP) .................... 19152310

(51) Int. Cl.
  *G01N 33/72*  (2006.01)
  *G01N 33/68*  (2006.01)
(52) U.S. Cl.
  CPC ....... *G01N 33/723* (2013.01); *G01N 33/6848* (2013.01)

(58) Field of Classification Search
CPC .................. G01N 33/6848; G01N 33/723
See application file for complete search history.

(56) References Cited

U.S. PATENT DOCUMENTS

| | | |
|---|---|---|
| 5,674,699 A | 10/1997 | Saunders et al. |
| 2018/0031578 A1 | 2/2018 | Eissa et al. |

FOREIGN PATENT DOCUMENTS

| | | |
|---|---|---|
| CN | 105445409 A | 3/2016 |
| JP | S61280571 A | 12/1986 |
| JP | H05-500111 A | 1/1993 |
| WO | 2008009445 A1 | 1/2008 |
| WO | 2017103180 A1 | 6/2017 |

OTHER PUBLICATIONS

Castillo, Quantitative targeted biomarker assay for glycated haemoglobin by multidimensional LC using mass spectrometric detection, 2011, Journal of Proteomics, 74, pp. 35-43. (Year: 2011).*
Espacenet English Translation of CN 105445409A. (Year: 2016).*
Benjamin et al., Glycated Protein Update: Implications of Recent Studies, Including the Diabetes Control and Complications Trial; Clin. Chem., 1994, vol. 40, No. 5, pp. 683-687.

(Continued)

*Primary Examiner* — Kathryn Elizabeth Limbaugh
(74) *Attorney, Agent, or Firm* — Taft Stettinius & Hollister LLP (57) ABSTRACT

The present invention refers to a method for determining intact glycated hemoglobin A (HbA1c) by mass spectrometry (MS), a kit and a diagnostic system adapted for performing the method.

16 Claims, 3 Drawing Sheets

(56) References Cited

OTHER PUBLICATIONS

Biroccio et al., A quantitative method for the analysis of glycated and glutathionylated hemoglobin by matrix-assisted laser desorption ionization-time of flight mass spectrometry; Analytical Biochemistry, 2005, vol. 336, pp. 279-288.

Davison et al., fetal hemoglobin: assessment of glycation and acetylation status by electrospray ionization mass spectrometry; Clin Chem Lab Med., 2008, vol. 46, No. 9, 10-pages.

Dupont et al., Determination of Glycated and Acetylated Hemoglobins in Cord Blood by Time-of-Flight Mass Spectrometry; Analytical Chemistry; 2011, vol. 83, pp. 5245-5252.

Goldstein et al., Is Glycohemoglobin Testing Useful in Diabetes Mellitus: Lessons form the Diabetes Control and Complications Trial; Clin. Chem., 1994, vol. 40, No. 8, pp. 1637-1640.

Hattan et al., Analysis and Quantitation of Glycated Hemoglobin by Matrix Assisted Laser Desorption/Ionization Time of Flight Mass Spectrometry; J. Am. Soc. Mass Spectrom., 2016, vol. 27, pp. 532-541.

Jeppsson et al., Approved IFCC Reference Method for the Measurement of HbA1c in Human Blood; Clin Chem Lab Med, 2002, vol. 40, No. 1, pp. 78-89.

Nathan et al., The Effect of Intensive Treatment of Diabetes n the Development and Progression of Long-Term Complications in Insulin-Dependent Diabetes Mellitus; The New England Journal of Medicine; 1993, vol. 329, No. 14, 10-pages.

Roberts et al., Potential of electrospray mass spectrometry for quantifying glycohemoglobin; Clinical Chemistry, 1997, 9-pages.

Jeong et al., Optimization of Enzyme Digestion Conditions for Quantification of Glyeated Hemoglobin Using Isotope Dilution Liquid Chromatography-Tandem Mass Sepctrometry; Mass Spectrometry Letters; 2014, vol. 5, No. 2, 5-pages.

Li et al., Association of serum lipid metabolism with markers of urinary peptides in type 2 diabetes patients; Int. J. Clin. Exp. Pathol., 2016, vol. 9, No. 1, pp. 37-48.

Li et al., Application of shielding boronate affinity chromatography in the study of the glycation pattern of haemoglobin; Journal of Chromatography B; 2002, vol. 776, pp. 149-160.

Santiago, J.V .; Perspectives in Diabetes; Lessons From the Diabetes Control and Complications Trial; Diabetes, 1993, vol. 42, 6-pages.

Willekens et al., Quantification of Glycohemoglobin in Blood by Mass Spectometry Applying Multiple-Reaction Monitoring; Clinical Chemistry, vol. 46, No. 2, 3-pages.

Zhang et al., Quantification of hemoglobin A1c by off-line HPLC separation and liquid chromatography-tandem mass spectrometry: a modification of the IFCC reference measurement procedure; Clin Chem Lab Med, 2016, vol. 54, No. 4, pp. 569-576.

Vesper, H.W. et al., Assessment of microwave-assisted enzymatic digestion by measuring glycated hemoglobin A1c by mass spectrometry, Rapid Commun. Mass Spectrom., 2005, pp. 2865-2870, vol. 19.

Japanese Office Action, Japan Patent Office, Japan Patent Application No. 2024-089775, Jan. 17, 2025, 6 pages.

\* cited by examiner

| Summe | | | Summen EICs | | |
|---|---|---|---|---|---|
| ohne Glc | mit Glc | mit Glc / ohn Glc | ohne Glc | mit Glc | mit Glc / ohn Glc |
| 107145 | 8976 | 0.084 | 107012 | 9138 | 0.085 |
| 111594 | 9733 | 0.087 | 111448 | 9759 | 0.088 |
| 108863 | 9426 | 0.087 | 108637 | 9597 | 0.088 |
| 117315 | 10296 | 0.088 | 117303 | 10376 | 0.088 |
| 115744 | 10305 | 0.089 | 115460 | 10480 | 0.091 |
| 118465 | 10261 | 0.087 | 118319 | 10610 | 0.090 |
| 108682 | 9476 | 0.087 | 108412 | 9648 | 0.089 |
| 116853 | 10140 | 0.087 | 116686 | 10245 | 0.088 |
| 113643 | 9791 | 0.086 | 113341 | 9949 | 0.088 |
| 111389 | 9758 | 0.088 | 111121 | 10024 | 0.090 |
| 112969.3 | 9816.2 | 0.087 | 112773.9 | 9982.6 | 0.088 |
| 3.56 | 4.50 | 1.56 | 3.60 | 4.59 | 1.74 |

AUTOMATIC SAMPLE WORKFLOW FOR LC-MS BASED HBA1C MEASUREMENT ON INTACT PROTEIN LEVEL

This application is a U.S. Continuation Application of International Application No. PCT/EP2020/051041 filed Jan. 16, 2020, claiming priority to European Application No. 19152310.9 filed Jan. 17, 2019, the disclosures of which are hereby incorporated by reference in their entirety.

DESCRIPTION

The present invention refers to a method for determining intact glycated hemoglobin A (HbA1c) molecules by mass spectrometry (MS), a kit, and a diagnostic system adapted for performing the method.

BACKGROUND OF THE INVENTION

Impaired control of circulating blood glucose levels is an indicator of diabetes. Blood glucose may attach in a non-enzymatic statistical process to the lysine residues of polypeptides thereby leading to glycated polypeptides. In the case of hemoglobin A (HbA), a reaction occurs between glucose and the N-terminus of the β-chain. The resulting glycated hemoglobin A β-chain has been designated as HbA1c.

HbA1c is the major glycated hemoglobin species in human blood. The comprehensive Diabetes Control and Complications Trial (DCCT) has provided evidence that complications such as retinopathy, nephropathy and neuropathy are directly related to the degree of hyperglycemia in patients with insulin-dependent diabetes (IDDM), and has shown that the measurement of HbA1c in blood is an excellent tool for long-term monitoring of the glycemic state of diabetes patients (Nathan et al., N. Engl. J. Med 329 (1993) 977-986; Santiago, J. V., Diabetes 42 (1993) 1549-1554; Benjamin, J. and Sacks, D. B., Clin. Chem. 40 (1994) 683-687; and Goldstein D. et al., Clin. Chem 40 (1994) 1637-1640). The DCCT study has also clearly demonstrated the need for reliable and reproducible measurement of HbA1c and HbA0—the non-glycated hemoglobin, respectively.

There are numerous different methods for determining glycated hemoglobin, namely physico-chemical methods including chromatography and/or mass spectrometry (MS), chemical methods and immunological methods. A reference method for the measurement of HbA1c in human blood which has been approved by the International Federation of Clinical Chemistry and Laboratory Medicine (IFCC) comprises enzymatic cleavage of hemoglobin into peptides by the enzyme endoproteinase Glu-C for a time period of 18-20 h and subsequently separating and quantifying glycated and non-glycated N-terminal hexapeptides of the β-chain by HPLC and electrospray ionization mass spectrometry or in a two-dimensional approach using HPLC and capillary electrophoresis with UV-detection (Jeppsson et al., Clin. Chem. Lab. Med. 40 (2002), 78-89).

Methods involving enzymatic digestion of hemoglobin A, however, usually require an overnight incubation in order to obtain a sufficient amount of cleavage products and thus stable measurement signals. Further, a separation of complex peptide mixtures including matrix components with conventional chromatography is required before subjecting the sample to the MS detection. These methods are thus time-consuming and of limited use for high-throughput measurements of patient samples.

Several attempts of determining glycated hemoglobins by MS using intact hemoglobin molecules have been described. According to Roberts et al. (Clin. Chem. 43 (1997), 771-778), whole blood samples were diluted 50-fold with water, then diluted further with an acidic denaturing solvent comprising formic acid and acetonitrile and directly introduced into the electrospray source of a mass spectrometer operated in the positive ion mode. The resulting spectra were processed to determine the percentage of glycated hemoglobin in the sample.

Biroccio et al. (Anal. Biochem. 336 (2005), 279-288) disclose a method for the analysis of intact glycated and glutathionylated hemoglobin by matrix-assisted laser desorption ionization time-of-flight MS. For this purpose, samples were prepared with a sandwich layer method in a sinapinic acid matrix comprising acetonitrile and trifluoroacetic acid.

Davison et al. (Clin. Chem. Lab. Med. 46 (2008), 1230-1238) describe electrospray ionization MS for the measurement of glycated and acetylated fetal hemoglobins. Blood samples were diluted in an acidic denaturing solvent comprising formic acid and acetonitrile. After washing with cation exchange beads to remove Na and K, the samples were directly introduced into the electrospray source of a mass spectrometer operated in the positive ion mode.

A determination of glycated and acetylated hemoglobins in cord blood by time-of-flight MS is described by Dupont et al. (Anal. Chem. 83 (2011), 5245-5252). Samples were prepared by diluting whole cord blood with water and adding a mixture comprising acetonitrile, water and formic acid. The final solution was treated with a cation exchange resin prior to injection into the mass spectrometer. Analyses were performed on a quadrupole orthogonal acceleration time-of-flight MS using an electrospray ionization source working in positive mode and W-Optics.

Hattan et al. (J. Am. Soc. Mass Spectrom. 27 (2016), 532-541) describe analysis and quantitative determination of glycated hemoglobin by matrix-assisted laser desorption/ionization time-of-flight MS. Whole blood samples were diluted in water and centrifuged. The supernatant was mixed with sinapinic acid and spotted on a MALDI target. Mass spectra were generated in linear, positive-ion mode on a MALDI-TOF mass spectrometer.

The above methods are, however, associated with disadvantages since they did not provide satisfactory and reproducible results. In particular, a high coefficient of variations was observed when repeatedly testing a given sample. Thus, there is a need for providing a rapid and reliable method for determining HbA1c by MS.

SUMMARY OF THE INVENTION

A first aspect of the present invention refers to a method for determining intact molecules of glycated hemoglobin A (HbA1c) in a sample, wherein the method comprises:
  (a) providing a sample comprising hemoglobin A (HbA) molecules, in particular intact HbA molecules,
  (b) enriching intact hemoglobin A, in particular the α- and/or the β-chain of hemoglobin A, molecules in said sample, and
  (c) subjecting the sample comprising intact hemoglobin A, in particular the α- and/or the β-chain of hemoglobin A, molecules to an analysis by mass spectrometry (MS), wherein the amount or concentration of HbA1c molecules in the sample is determined.

A second aspect of the present invention refers to a kit, comprising (i) enrichment means for enriching intact glycated HbA1c molecules, in particular comprising a solid phase having a hydrophobic surface for selective binding of intact glycated HbA1c molecules, (ii) a substantially neutral solid phase binding medium for use in diluting a hemolysed whole blood sample and binding sample constituents to the solid phase (i) and (iii) an elution medium comprising an organic water-miscible solvent such as acetonitrile, particularly in an amount of about 20% to about 60% (v/v), in particular in an amount of about 50% (v/v) for use in eluting sample components from the enrichment means (i).

The kit is particularly suitable for use in a method as described above.

In a third aspect of the invention a diagnostic system is provided which is adapted for performing the method as described above. The diagnostic system is particularly for use together with the kit as described above.

The present invention allows rapid and reliable determination of intact glycated HbA1c molecules and optionally of intact non-glycated HbA0 molecules in a sample by MS.

DETAILED DESCRIPTION

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include the respective terms also in plural, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "Mass Spectrometry" ("Mass Spec" or "MS") relates to an analytical technology used to identify compounds by their mass. MS is a method of filtering, detecting, and measuring ions based on their mass-to-charge ratio, or "m/z". MS technology generally includes (1) ionizing compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net electrical charge equal to one or more electron units. Negative ions are those having a net negative charge of one or more electron units, while positive ions are those having a net positive charge of one or more electron units. The MS method may be performed either in "negative ion mode", wherein negative ions are generated and detected, or in "positive ion mode" wherein positive ions are generated and detected.

"Time-of-flight" (TOF) MS is a method wherein an ion's mass-to-charge ratio is determined via a time of flight measurement. Ions are accelerated by an electric field of known strength. The velocity of the ion depends on the mass-to-charge ratio. The time for ion to reach a detector at a known distance is measured. Based on this measurement, the ion can be identified.

Most sample workflows in MS further include sample preparation and/or enrichment steps, wherein e.g. the analyte(s) of interest are separated from the matrix, e.g. sample constituents different from the analyte, using e.g. gas or liquid chromatography. Typically, for the mass spectrometry measurement, the following three steps are performed:

(1.) a sample comprising an analyte of interest is ionized, usually by adduct formation with cations, often by protonation to cations. Ionization sources include but are not limited to electrospray ionization (ESI) and atmospheric pressure chemical ionization (APCI).

(2.) the ions are sorted and separated according to their mass and charge. High-field asymmetric-waveform ion-mobility spectrometry (FAIMS) may be used as ion filter.

(3.) the separated ions are then detected, e.g. in multiple reaction mode (MRM), and the results are displayed on a chart.

The term "electrospray ionization" or "ESI," refers to methods in which a solution is passed along a short length of capillary tube, to the end of which is applied a high positive or negative electric potential. A solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. The ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar entity.

"Multiple reaction mode" or "MRM" is a detection mode for a MS instrument in which a precursor ion and one or more fragment ions are selectively detected.

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Mass spectrometric determination may be combined with additional analytical methods including chromatographic methods such as gas chromatography (GC), liquid chromatography (LC), particularly HPLC, and/or ion mobility-based separation techniques.

In the context of the present disclosure, the terms "analyte", "analyte molecule", or "analyte(s) of interest" are used interchangeably referring to the chemical species to be analysed via mass spectrometry. Chemical species suitable to be analysed via mass spectrometry, i.e. analytes, can be any kind of molecule present in a living organism, include but are not limited to nucleic acids (e.g. DNA, mRNA, miRNA, rRNA etc.), amino acids, peptides, proteins (e.g. cell surface receptor, cytosolic protein etc.), metabolites or hormones (e.g. testosterone, estrogen, estradiol, etc.), fatty acids, lipids, carbohydrates, steroids, ketosteroids, secosteroids (e.g. Vitamin D), molecules characteristic of a certain modification of another molecule (e.g. sugar moieties or phosphoryl residues on proteins, methyl-residues on genomic DNA) or a substance that has been internalized by the organism (e.g. therapeutic drugs, drugs of abuse, toxin, etc.) or a metabolite of such a substance. Such analyte may serve as a biomarker. In the context of present invention, the term "biomarker" refers to a substance within a biological system that is used as an indicator of a biological state of said system.

Analytes may be present in a sample of interest, e.g. a biological or clinical sample. The terms "sample" or "sample of interest" are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, spinal fluid, urine, saliva, and lymphatic fluid, or solid samples such as dried blood spots and tissue extracts. Further examples of samples are cell cultures or tissue cultures.

In the context of the present disclosure, the sample may be derived from an "individual" or "subject". Typically, the subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

Before being analysed via Mass Spectrometry, a sample may be pre-treated in a sample- and/or analyte specific manner. In the context of the present disclosure, the term "pre-treatment" refers to any measures required to allow for the subsequent analysis of a desired analyte via Mass Spectrometry. Pre-treatment measures typically include but are not limited to the elution of solid samples (e.g. elution of dried blood spots), the addition of a hemolyzing reagent (HR) to whole blood samples, and the addition of an enzymatic reagent to urine samples. Also the addition of internal standards (ISTD) is considered as pre-treatment of the sample.

The term "hemolysis reagent" (HR) refers to reagents which lyse cells present in a sample. In the context of this invention hemolysis reagents in particular refer to reagents which lyse the cells present in a blood sample including but not limited to the erythrocytes present in whole blood samples. A well-known hemolysis reagent is water ($H_2O$), e.g. deionized or distilled water. Further examples of hemolysis reagents include but are not limited to liquids with high osmolarity (e.g. 8M urea), ionic liquids, and different detergents.

Typically, an internal standard (ISTD) is a known amount of a substance which exhibits similar properties as the analyte of interest when subjected to the mass spectrometric detection workflow (i.e. including any pre-treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass-spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer. Typically, but not necessarily, the ISTD is an isotopically labeled variant (comprising e.g. at least one $^2H$, $^{13}C$, and/or $^{15}N$ etc. label) of the analyte of interest.

In addition to the pre-treatment, the sample may also be subjected to one or more enrichment steps, wherein the sample is subjected to one or more "enrichment methods" or "enrichment workflows". Well-known enrichment methods include but are not limited to chemical precipitation, the use of a solid phase, and chromatographic methods.

Chemical precipitation refers to the addition of chemical components to the sample, which cause certain constituents of the sample to participate. Exemplified, a well-known precipitation method is the addition of acetonitrile to the sample.

Solid phases include but are not limited to Solid Phase Extraction (SPE) cartridges, and beads. The term "bead" refers to non-magnetic, magnetic, or paramagnetic spherical particles. Beads may be coated differently to be specific for an analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores.

The term "chromatography" refers to a process in which a chemical mixture carried by a liquid or gas is separated into components as a result of differential distribution of the chemical entities as they flow around or over a stationary liquid or solid phase.

The term "liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) are termed reversed phase liquid chromatography (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarities of the mobile and stationary phases, namely NP-HPLC and RP-HPLC.

Micro LC refers to a HPLC method using a column having a narrow inner column diameter, typically below 1 mm, e.g. about 0.5 mm. "Ultra high performance liquid chromatography" or "UHPLC" refers to a HPLC method using a high pressure of e.g. 120 MPa (17,405 lbf/in$^2$), or about 1200 atmospheres.

Rapid LC refers to an LC method using a column having an inner diameter as mentioned above, with a short length <2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time <1 min.

Further well-known LC modi include Hydrophilic interaction chromatography (HIC), size-exclusion LC, ion exchange LC, and affinity LC.

LC separation may be single-channel LC or multi-channel LC comprising a plurality of LC channels arranged in parallel. In LC analytes may be separated according to their polarity or log P value, size or affinity, as generally known to the skilled person.

In the context of the present disclosure, the term "first enrichment process", "first enrichment step", or "first enrichment workflow" refers to an enrichment process which occurs subsequent to the pre-treatment of the sample and provides a sample comprising an enriched analyte relative to the initial sample.

In the context of the present disclosure the term "second enrichment process", "second enrichment step", or "second enrichment workflow" refers to an enrichment process which occurs subsequent to the pre-treatment and the first enrichment process of the sample and provides a sample comprising an enriched analyte relative to the initial sample and the sample after the first enrichment process.

A "kit" is any manufacture article (e.g. a package or container) comprising at least one reagent, e.g., a medicament for treatment of a disorder, or a probe for specifically detecting an analyte of the present invention. The kit is preferably promoted, distributed, or sold as a unit for performing the method of the present invention. Typically, a kit may further comprise carrier means being compartmentalized to receive in close confinement one or more container means such as vials, tubes, and the like. In particular, a container means may comprise one of the separate elements to be used in the method of the first aspect. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The kit may also include a computer program code provided on a data storage medium or device such as an optical storage medium (e.g., a Compact Disc) or directly on a computer or data processing device. Moreover, the kit may comprise standard amounts for the biomarkers as described elsewhere herein for calibration purposes.

A "package insert" is used to refer to instructions customarily included in commercial packages of diagnostic products, that contain information about the indications, usage, performance, and/or warnings concerning the use of such diagnostic product.

Embodiments

A first aspect of the present invention refers to a method for determining intact molecules of glycated hemoglobin A (HbA1c) in a sample, comprising:
  (a) providing a sample comprising hemoglobin A (HbA) molecules, in particular intact hemoglobin A (HbA) molecules,
  (b) enriching the hemoglobin A molecules, in particular the α-chain and/or the β-chain molecules, in said sample, and
  (c) subjecting the sample comprising intact hemoglobin A molecules, in particular the α-chain and/or the β-chain molecules, to an analysis by mass-spectrometry (MS) wherein the amount or concentration of HbA1c in the sample is determined.

Thereby, the amount or concentration of HbA1c, in particular the relative amount of HbA1c, i.e. the ratio of glycated HbA1c molecules to non-glycated HbA0 molecules or to HbA molecules in total, in a sample can be determined. The method is highly accurate and may give coefficient of variation (CV) of 2.5% or less, more particularly of 2.0% or less when repeatedly determining the amount of HbA1c, the ratio of HbA1c/HbA, or the ratio HbA1c/HbA0 in a given sample.

According to step (a) a sample comprising hemoglobin molecules is provided. The sample is preferably a hemolysed whole blood sample, particularly a hemolysed human whole blood sample, e.g. derived from a subject the blood of which to be tested for the amount of glycated hemoglobin A. Hemolysis is particularly carried out by dilution with water ($H_2O$), e.g. deionized or distilled water, in particular in a ratio of sample:water of about 1:2 to about 1:20, e.g. of about 1:5, about 1:10, or in particular about 1:9 (v/v). The sample may be hemolysed for a time less than about 30 min, less than about 10 min, less than about 5 min or even less than about 2 min. In particular embodiments, the sample is hemolyzed for a time of about 10 to about 60 sec.

In particular embodiments, the hemolysis is carried out by mixing sample and water, in particular by vortexing sample and water. In particular sample and water are mixed, in particular vortexed, for 1 to 60 sec, in particular for 5 to 30 sec, in particular for 10 sec.

During hemolysis the sample may be kept at a temperature of 20° C. to 30° C., in particular at 22-25° C., in particular at room temperature.

In particular embodiments, the hemolysis of the sample is carried out by mixing the sample with water in a ratio of 1:9 by vortexing for 10 sec at room temperature.

In particular embodiments, the sample obtained in step (a) is subjected to an enrichment workflow, i.e. the enrichment step (b) which comprises enriching of intact hemoglobin A molecules, in particular the α- and/or the-β-chains molecules, in the sample. The enrichment step increases the relative amount of intact hemoglobin A molecules, in particular the α- and/or the β-chain of hemoglobin A molecules, versus other sample constituents before subjecting the sample into analysis by MS.

In particular embodiments, the enrichment step (b) comprises an enrichment of intact hemoglobin A β-chain molecules versus hemoglobin A α-chain molecules, particularly by at least a factor of about 2 by at least a factor of about 5 or by at least a factor of about 10, and/or an enrichment of intact hemoglobin A β-chain molecules versus albumin molecules, particularly by at least a factor of about 2, by at least a factor of about 5 or by at least a factor of about 10.

The enrichment step (b) may include one or more enrichment methods, in particular a first and/or a second enrichment step. Enrichment methods are well-known in the art and include but are not limited to chemical enrichment methods including but not limited to chemical precipitation, and enrichment methods using solid phases including but not limited to solid phase extraction methods, bead workflows, and chromatographic methods (e.g. gas or liquid chromatography). Accordingly, in particular embodiments, enrichment step (b) comprise one or more enrichment methods selected from the group consisting of chemical precipitation, methods using solid phase extraction methods, bead workflows, and chromatographic methods.

In embodiments, enrichment step (b) comprises one or two enrichment methods, i.e. comprises enrichment step (b)(i) and/or enrichment step (b)(ii). In embodiments, wherein the method comprises enrichment step (b)(i) and enrichment step (b)(ii), enrichment step (b)(i) is performed prior to enrichment step (b)(ii).

In embodiments, enrichment step (b)(i) comprises a bound/free separation step comprising the addition of a solid phase carrying analyte-selective groups to the pre-treated sample. The solid phase may be comprised of solid particles or of a non-particular solid phase, e.g. a coated surface within a vessel or a well. In particular embodiments, the solid phase is comprised of magnetic or paramagnetic particles, in particular particles having a magnetic or paramagnetic core. In embodiments, said magnetic or paramagnetic core comprises a metal oxide and/or a metal carbide. In an especially particular embodiment, the core comprises $Fe_3O_4$.

The surface of the solid phase, in particular the magnetic or paramagnetic beads, may be a hydrophobic surface, in particular comprising hydrophobic organic groups such as $C_3$-$C_{18}$ alkyl groups, more particularly $C_4$ alkyl groups. Further, the hydrophobic surface of the solid phase, in particular the surface of the magnetic or paramagnetic beads, comprises pores. The pore size may be in the range of from 1 nm to 200 nm, in particular less than about 100 nm, in particular less than about 10 nm. Suitable hydrophobic surfaces may e.g. be found in "The HPLC Expert: Possibilities and Limitations of Modern High Performance Liquid Chromatography" D01:10.1002/9783527677610.

In embodiments, enrichment step (b) comprises a first enrichment step (b)(i), using magnetic or paramagnetic beads. In embodiments, the first enrichment step (b)(i) comprises the addition of magnetic or paramagnetic beads carrying groups for the selective binding of intact hemoglobin A molecules, in particular the α- and/or the β-chain of hemoglobin A, present in the sample. In embodiments, the addition of the magnetic beads comprises agitation or mixing. A pre-defined incubation period for capturing the intact hemoglobin A molecules, in particular the α- and/or the β-chain of hemoglobin A, on the bead follows. In embodiments, the workflow comprises a washing step (W1) after incubation with the magnetic beads. Depending on the analyte(s) one or more additional washing steps (W2) are performed. One washing step (W1, W2) comprises a series of steps including magnetic bead separation by a magnetic bead handling unit comprising magnets or electromagnets, aspiration of liquid, addition of a washing buffer, resuspension of the magnetic beads, another magnetic bead separation step and another aspiration of the liquid. Moreover, washing steps may differ in terms of type of solvent (water/organic/salt/pH), apart from volume and number or combination of washing cycles. It is well-known to the skilled person how to choose the respective parameters. The last of the washing steps (W1, W2) is followed by the addition of an elution reagent followed by resuspension of the magnetic beads and a pre-defined incubation period for releasing the analyte(s) of interest from the magnetic beads. The bound-free magnetic beads are then separated and the supernatant containing intact hemoglobin A molecules, in particular the α- and/or the β-chain of hemoglobin A, is captured.

In particular embodiments, contacting of the sample comprising intact hemoglobin A molecules, in particular the α- and/or the β-chain of hemoglobin A, with the solid phase takes place at a substantially neutral pH, e.g. at a pH of about 5 to about 7, particularly at a pH of about 6. For this purpose, a sample, e.g. a hemolysed whole blood sample, may be diluted in a solid phase binding medium. The buffer is preferably a buffer which does not comprise $Na^+$ or $K^+$ ions, e.g. a buffer comprising ammonium, mono-, di- or tri-substituted ammonium ions. The anion is preferably a carboxylate anion such as formate. An especially preferred buffer is ammonium formate, e.g. an ammonium formate buffer of pH 6.

Selective elution of bound constituents from the solid phase may be performed by contacting the solid phase loaded with sample constituents with an elution medium comprising an organic water-miscible solvent, e.g. an aprotic solvent such as acetonitrile, in an amount of 20 to 60% (v/v), in particular in an amount of about 20, 30, 40, or 50% (v/v). The pH of the elution medium and the constituents of the aqueous portion of the elution medium may be the same as described for the solid phase binding medium.

Alternatively or additionally, enrichment step (b) may comprise a second enrichment step (b)(ii). In the second enrichment step (b)(ii), intact hemoglobin A molecules, in particular the α- and/or the δ-chain of hemoglobin A, is further enriched in the sample. In particular embodiments, enrichment step (b)(ii) comprises a chromatographic step, wherein individual constituents of the sample are separated from each other. In particular, in the second enrichment step (b)(ii), the α- and the β-chain of hemoglobin A are separated from each other. In embodiments, the second enrichment step (b)(ii) may be performed subsequently to the first enrichment step (b)(i) as described in detail above.

In embodiments, the chromatographic separation is gas or liquid chromatography. Both methods are well known to the skilled person. In embodiments, the liquid chromatography is selected from the group consisting of HPLC, rapid LC, micro-LC, flow injection, and trap and elute. In particular embodiments, the chromatographic separation comprises the use of a single chromatic column, or the use of two or more chromatic columns. In particular embodiments, wherein two or more chromatic columns are used, the columns are positioned downstream of each other, i.e. a second column is positioned downstream of a first column, and an optional third column is position downstream of the second column, etc. In embodiments wherein two or more columns are used, these columns may be identical or may differ from each other depending on the desired function. It is well-known to the skilled person to choose the correct columns and set up.

In embodiments, the sample obtained after hemolysis in step (a) or the first enrichment step (b)(i) is transferred to an LC station or is transferred to the LC station after a dilution step by addition of a dilution liquid. Different elution procedures/reagents may also be used, by changing e.g. the type of solvents (water/organic/salt/pH) and volume. The various parameters are well-known to the skilled person and easily chosen.

In certain embodiments, enrichment step (b) comprises a first enrichment step (b)(i) and a second enrichment step (b)(ii), wherein the second enrichment step (b)(ii) is performed subsequent to the first enrichment step (b)(i). In particular embodiments, the first enrichment step (b)(i) comprises bead workflow as described in detail above, and the second enrichment step (b)(ii) comprises liquid chromatography, in particular selected from the group consisting of HPLC, rapid LC, micro-LC, flow injection, and/or trap and elute.

According to the present invention, step (c) of the method of the present invention comprises an analysis of intact hemoglobin A molecules, in particular the α- and/or the β-chain of hemoglobin A, i.e. an analysis of an intact hemoglobin A molecules, in particular the α- and/or the β-chain of hemoglobin A, molecules which have not been subjected to digestion with a protease such as trypsin or Glu-C.

The analysis according to step (c) of is carried out by MS. In principle, different MS analysis procedures may be used. Preferably the MS analysis procedure comprises a time-of-flight (TOF) MS analysis, particularly a quadrupole (Q) TOF MS analysis. Further it is preferred that the MS analysis is carried out in the positive mode and/or a signal integration of several charge states of intact hemoglobin A β-chain molecule, particularly including charge states from M+17H to M+13H is carried out.

The method of the invention comprises a quantitative determination of HbA1c in the sample. In particular, the relative amount of glycated HbA1c molecules to non-glycated HbA0 molecules or to HbA molecules in total is determined. In an especially preferred embodiment, this relative amount is determined with a coefficient of variation (CV) of 2.5% or less, particularly of 2.0% or less.

In an especially preferred embodiment, the method of the invention comprises a workflow as follows:
  (a) hemolysing a whole blood sample, e.g. by dilution with $H_2O$,
  (b) enriching intact hemoglobin A molecules, in particular the α- and the β-chain of hemoglobin A, in the hemolysed sample generated in step (a) by contacting the sample with a solid phase, particularly comprised of magnetic or paramagnetic particles, having a hydrophobic surface under conditions wherein intact hemoglobin A β-chain molecules bind to the solid phase, and selectively eluting the bound molecules from the loaded solid phase, and
  (c) subjecting the sample from step (b) comprising intact hemoglobin A β-chain molecules to an analysis by TOF-MS wherein the amount or concentration of HbA1c in the sample is determined.

In particular embodiments, this workflow allows for high throughput analysis of more than 100 samples per hour.

In an especially preferred embodiment, the method of the invention comprises a workflow as follows:
  (a) hemolysing a whole blood sample, e.g. by dilution with $H_2O$,
  (b) enriching intact hemoglobin A molecules, in particular the β-chain of hemoglobin A, in the hemolysed sample generated in step (a) by subjecting the sample to liquid chromatography, in particular to HPLC or rapid LC under conditions wherein intact hemoglobin A β-chain molecules bind to the solid phase, and selectively eluting the bound molecules from the loaded solid phase, and
  (c) subjecting the sample from step (b) comprising intact hemoglobin A molecules to an analysis by TOF-MS wherein the amount or concentration of HbA1c in the sample is determined.

In particular embodiments, this workflow allows for the specific separation of the α- and the β-chain of hemoglobin A.

In an especially preferred embodiment, the method of the invention comprises a workflow as follows:
  (a) hemolysing a whole blood sample, e.g. by dilution with $H_2O$,
  (b) (i) enriching intact hemoglobin A molecules, in particular the α- and the β-chain of hemoglobin A, in the hemolysed sample generated in step (a) by contacting the sample with a solid phase, particularly comprised of magnetic or paramagnetic particles, having a hydrophobic surface under conditions wherein intact hemoglobin A α-chain molecules bind to the solid phase, and selectively eluting the bound molecules from the loaded solid phase, and
  (ii) further enriching intact hemoglobin A molecules, in particular the β-chain of hemoglobin A, in the hemolysed sample generated in step (b)(i) by subjecting the sample to liquid chromatography, in particular to HPLC or rapid LC under conditions wherein intact hemoglobin A β-chain molecules bind to the solid phase, and selectively eluting the bound molecules from the loaded solid phase, and (c) subjecting the sample from step (b) comprising intact hemoglobin A molecules to an analysis by TOF-MS wherein the amount or concentration of HbA1c in the sample is determined.

In further embodiments of the first aspect, the method of determining glycated hemoglobin A (HbA1c) in a sample comprises the additional step of adding an internal standard to the sample (ISTD). The internal standard is preferably an isotopically labeled HbA1c molecule. In embodiments the isotopically labeled ISTD comprises at least one $^2$H, $^{13}$C, and/or $^{15}$N label.

A second aspect of the present invention refers to a kit, comprising
  (i) enrichment means for enriching intact glycated HbA1c molecules, in particular a solid phase having a hydrophobic surface for selective binding of intact glycated HbA1c molecules,
  (ii) a substantially neutral solid phase binding medium for use in diluting a hemolysed whole blood sample and binding sample constituents to the solid phase (i), and
  (iii) an elution medium comprising an organic water-miscible solvent such as a acetonitrile, particularly in an amount of 20 to 60% (v/v), in particular in an amount of about 20, 30, 40, or 50% (v/v) for use in eluting sample components from the enrichment means (i).

With regard to particular embodiments of the second aspect of the present invention, reference is made to all embodiments described above in detail in context with the first aspect.

In embodiments, the kit comprises (i) a solid phase, e.g. particles such as particles having a hydrophobically modified surface, (ii) a substantially neutral solid phase binding medium, e.g. a buffer without Na$^+$ and K$^+$ ions, for use in diluting a hemolysed whole blood sample and binding sample constituents to the solid phase (i), and (iii) an medium buffer comprising an organic water-miscible solvent such as a acetonitrile in an amount of 20 to 60% (v/v), in particular in an amount of about 20, 30, 40, or 50% (v/v) for use in eluting sample components from the solid phase (i).

In embodiments, the kit comprises enrichment means adapted for carrying out at least one enrichment step, in particular a bound/free separation step and/or a chromatographic step. In embodiments, the enrichment means comprises a solid phase which may be comprised of solid particles, e.g. magnetic or paramagnetic particles, or of a non-particular solid phase.

In particular embodiments, the solid phase carries groups for the selective binding of intact hemoglobin A molecules, in particular the α- and/or the β-chain of hemoglobin A, molecules, e.g. hydrophobic organic groups. In further particular embodiments, the enrichment means may comprise a chromatographic column, in particular a chromatographic column for performing a chromatographic step.

In embodiments, the elution medium optionally comprised in the kit comprises an aqueous solution comprising an organic water-miscible solvent, in particular acetonitrile (ACN). The organic water-miscible solvent, in particular the ACN is present in an amount of about 20 to 60% (v/v), in particular in an amount of about 20, 30, 40, or 50% (v/v).

The kit may be provided as a single package comprising containers of the individual components or as a set of several packages each comprising a container of the individual components.

In embodiments, the kit further comprises a package insert. In embodiments, the package insert comprises information on the indications, usage, performance, and/or warnings concerning the kit.

A third aspect of the present invention is a diagnostic system adapted for determining glycated HbA1c in a sample; in particular by performing the method as described above.

In particular embodiments, the diagnostic system comprises:
  (i) at least one station for the preparation of samples comprising intact of HbA1c molecules, in particular wherein the preparation comprising a hemolysis of a whole blood sample,
  (ii) at least one enrichment station adapted for selectively enriching intact hemoglobin A molecules, in particular the α- and/or the β-chain of hemoglobin A, from the sample, and
  (iii) at least one station adapted for the analysis of intact hemoglobin A molecules, in particular the α- and/or the β-chain of hemoglobin A, by mass-spectrometry (MS) and determining the amount or concentration of HbAc1 in the sample.

With regard to particular embodiments of the third aspect of the present invention, reference is made to all embodiments described above in detail in context with the first and second aspect.

In particular embodiments, the diagnostic system is adapted for allowing a high-throughput of samples, in particular for allowing a throughput of up to 100 samples/hour or more. For example, a system as described in WO 2017/103180, incorporated herein by reference, may be used.

In particular embodiments, the diagnostic system comprises at least one station for random access sample preparation, and at least one station for the enrichment of the intact hemoglobin A molecules, in particular the α- and/or the β-chain of hemoglobin A, before MS analysis.

In embodiments, such a diagnostic system comprises a sample preparation station for the automated preparation of samples comprising intact hemoglobin A molecules, in particular the α- and/or the β-chain of hemoglobin A. In particular embodiments, said station comprises a section for hemolysing one or more samples.

In embodiments, said diagnostic system further comprises an enrichment station. Said enrichment station comprises a section for contacting one or more samples after hemolysis with enrichment means, in particular with a solid phase, in particular magnetic or paramagnetic particles. Additionally or alternatively, the enrichment station comprises a chromatographic section, in particular an LC section. In embodiments, the LC section comprises one or more LC channels. In embodiments, wherein the LC section comprises more than one LC channel, the channels may be arranged in parallel.

In embodiments, the diagnostic system comprises at least one interface between the different sections and stations for inputting the previously prepared samples into the subsequent section or station.

In embodiments, the diagnostic system further comprises a controller which may be programmed to assign samples to pre-defined sample preparation and enrichment workflows each comprising a pre-defined sequence of sample preparation and enrichments steps and requiring a pre-defined time for completion.

In particular embodiments, the controller plans an enrichment station channel input sequence for inputting the prepared samples that allows intact HbA β-chain molecules from different enrichment station channels to elute in a non-overlapping eluate output sequence based on expected elution times.

In embodiments, the controller sets and initiates a sample preparation start sequence that generates a prepared sample output sequence out of the sample preparation station that matches the enrichment station channel input sequence so that when preparation of a sample is completed the assigned enrichment station channel is also available and the prepared sample can be inputted into the assigned enrichment station channel, before preparation of another sample is completed or before the next prepared sample arrives to the sample preparation/enrichment interface.

In embodiments, the controller sets a reference period for the appropriate timing of workflows. This makes it possible to coordinate the following processing steps: (1) start preparation of at most one sample per reference period with possible one or more reference periods between consecutive samples in the sample preparation start sequence; and/or (2) complete preparation of at most one sample per reference period with possible one or more reference periods between consecutive prepared samples of the prepared sample output sequence; and/or (3) input one prepared sample per reference period into one of the enrichment station channels with possible one or more reference periods between consecutive enrichment station channel inputs; and/or (4) output one enrichment station eluate per reference period with possible one or more reference periods between consecutive enrichment station eluates.

Further, the present invention relates to the following items:

1. A method for determining glycated hemoglobin A (HbA1c) in a sample, comprising:
   (a) providing a sample comprising hemoglobin A (HbA) molecules, in particular intact hemoglobin A (HbA),
   (b) enriching intact hemoglobin A, in particular the α- and/or the β-chain of hemoglobin A, molecules in said sample, and
   (c) subjecting the sample comprising intact hemoglobin A, in particular the α- and/or the β-chain of hemoglobin A, molecules to an analysis by mass spectrometry (MS), wherein the amount or concentration of HbA1c molecules in the sample is determined.

2. The method of item 1, wherein the sample in step (a) is a hemolysed whole-blood sample, particularly a hemolysed human whole-blood sample.

3. The method of item 1 or 2, wherein the sample in step (a) is hemolysed using water ($H_2O$), in particular in a ratio of sample:water of 1:2 to 1:20 (v/v), such as in a ratio of about 1:5 to about 1:10, or in a ratio of about 1:5, 1:6, 1:7, 1:8, 1:9, or 1:10 (v/v).

4. The method of any one of items 1-3, wherein the sample is hemolysed for a time period less than about 30 min, less than about 10 min, less than about 5 min, or less than about 2 min, in particular for a time of about 10 to about 60 sec.

5. The method of any one of items 1-4, wherein enrichment step (b) comprises a first enrichment step (in particular a bound/free separation step) (b)(i), in particular comprising contacting the sample with a solid phase having a surface for the selective binding of intact hemoglobin A, in particular the α- and the β-chain of hemoglobin A, under conditions wherein the intact hemoglobin A, in particular the α- and the β-chain of hemoglobin A, bind to the solid phase, and selectively eluting the bound hemoglobin A, in particular the α- and/or the β-chain of hemoglobin A, from the solid phase.

6. The method of item 5, wherein the solid phase comprises a hydrophobic surface.

7. The method of item 5 or 6, wherein in step (b)(i), the sample is contacted with the solid phase at a pH of about 5 to about 7, particularly at a pH of about 6.

8. The method of any one of items 5-7, wherein in step (b)(i), the sample is contacted with the solid phase in the presence of a buffer, in particular in the presence of ammonium formate.

9. The method of any one of items 5-8, wherein the solid phase is comprised of particles, in particular of magnetic or paramagnetic particles, in particular of particles having a magnetic or paramagnetic core comprising a metal oxide and/or a metal carbide, in particular $Fe_3O_4$.

10. The method of any one of items 5-9, wherein the hydrophobic surface of the solid phase comprises $C_3$-$C_{18}$ alkyl groups, particularly $C_4$ alkyl groups.

11. The method of any one of items 5-10, wherein the hydrophobic surface of the solid phase comprises pores having a pore size of less than about 100 nm, in particular less than about 10 nm.

12. The method of any one of items 5-11, wherein in enrichment step (b)(i), intact hemoglobin A, in particular the α- and the β-chain of hemoglobin A, molecules are enriched by selective elution from the solid phase, particularly in the presence of 20% to 60% (v/v) acetonitrile, more particularly in the presence of about 50% (v/v) acetonitrile.

13. The method of any one of items 1-12, wherein enrichment step (b) comprises a second enrichment step (b)(ii), in particular a chromatographic step (b)(ii), in particular liquid chromatography (LC), in particular selected from the group consisting of HPLC, micro-LC, and rapid LC, of the sample.

14. The method of any one of items 5-13 wherein enrichment step (b) comprises a bound/free separation step (b)(i) and a chromatographic step (b) (ii).

15. The method of any one of items 13-14, wherein in the chromatographic enrichment step (b)(ii), intact hemoglobin A β-chain molecules are enriched versus hemoglobin A α-chain molecules, particularly by at least a factor of 10, and/or intact hemoglobin A β-chain molecules are enriched versus albumin molecules, particularly by at least a factor of 10.

16. The method of any one of items 1-15, wherein step (c) comprises an analysis of intact hemoglobin A β-chain molecules, in particular wherein the intact hemoglobin A β-chain molecules have not been subjected to digestion by a protease, such as trypsin or Glu-C.

17. The method of any one of items 1-16, wherein step (c) comprises a time-of-flight (TOF) MS analysis, in particular a quadrupole (Q)-TOF MS analysis of intact hemoglobin A β-chain molecules.

18. The method of any one of items 1-16, wherein determining the amount of HbA1c in the sample comprises signal integration of several charged states of intact hemoglobin A β-chain molecules, particularly including charged states M+17H to M+13H.

19. The method of any one of items 1-18, wherein the ratio of glycated hemoglobin A (HbA1c) to non-glycated hemoglobin A (HbA0) or total hemoglobin A (HbA) is determined.

20. The method of any one of items 1-19, wherein the ratio is determined with a coefficient of variation (CV) of 2.5% or less, particularly of 2.0% or less.

21. A kit comprising
   (i) enrichment means for enriching intact glycated HbA1c molecules, in particular comprising a solid phase having a hydrophobic surface for selective binding of intact glycated HbA1c molecules, (ii) a substantially neutral solid phase binding medium for use in diluting a hemolysed whole blood sample and binding sample constituents to the solid phase (i) and (iii) an elution medium comprising an organic water-miscible solvent such as a acetonitrile, particularly in an amount of 50% (v/v) for use in eluting sample components from the enrichment means (i).

22. Use of the kit of item 21 in a method of any one of item 1-20.

23. A diagnostic system for determining glycated hemoglobin A (HbA1c) in a sample adapted for performing the method of any one of items 1-20.

24. A diagnostic system for determining glycated hemoglobin A (HbAc1) in a sample comprising (i) at least one station for the preparation of samples comprising intact HbA1c molecules, wherein the preparation comprises hemolysis of a whole blood sample, (ii) at least one enrichment station adapted for selectively enriching intact hemoglobin A molecules, in particular the α- and/or the β-chain of hemoglobin A, from the sample, and (iii) at least one station adapted for the analysis of intact hemoglobin A molecules, in particular the β-chain of hemoglobin A, by mass-spectrometry (MS) and determining the amount or concentration of HbAc1 in the sample.

25. Use of the diagnostic system of item 23 or 24 in the method of any one of items 1-20.

In the following, the present invention is explained in more detail by the Examples.

EXAMPLES

Example 1

Determination of Intact HbA1c in Whole Blood

Three whole blood samples of 100 μL were each diluted with 400 μL deionized water and mixed by vortex for 10 s until clear solutions were obtained. Then, each of the hemolysates was diluted 20-fold in a different buffer having a pH of 2, 6 or 10, respectively.

Three batches of hydrophobic magnetic beads (each 100 μL) were equilibrated by mixing with 900 μL of each of the three different buffers as indicated above. Subsequently, 900 μL supernatant were discarded and the equilibrated beads recovered.

Three 900 μL whole blood hemolysates samples (already diluted in three different buffers as indicated above) where added to the respective batch of equilibrated beads in order to obtain loaded beads. Then the mixtures were shaken at 37° C. and 1200 rpm for 15 min.

From the loaded beads a series of several fractions for LC-MS was collected as follows:

First, 900 μL supernatant were collected from each batch of loaded beads. 100 μL of this "0% fraction" were ten-fold diluted by adding 900 μL 0.1% (v/v) formic acid (eluent A) for LC-MS. The beads were retained for collecting further fractions.

Next, a "10% fraction" was collected by adding 700 μL of the respective buffer and 200 μL 50% (v/v) acetonitrile (ACN) to each batch of beads. The mixtures were shaken at 37° C. at 1200 rpm for 1 min.

900 μL of the "10% fraction" were collected 100 μL were subsequently ten-fold diluted in 0.1% (v/v) formic acid for LC-MS.

Subsequently, this procedure was analogously repeated for each batch of loaded beads with buffers containing increasing concentrations of 20% (v/v), 30% (v/v) and 40% (v/v) ACN in order to obtain a "20% fraction", a "30% fraction" and a "40% fraction".

The resulting fractions, the 0% fraction, the 10% fraction, the 20% fraction, the 30% fraction and the 40% fraction from each batch of loaded beads were subjected to LC-MS analysis.

LC-MS measurements were performed on a Waters Synapt G2-Si HDMS QuanTof device. An ammonium formate buffer system and optimized source parameters were used for intact protein measurements. The ion transmission was optimized to eliminate chemical noise without HbA1c fragmentation. A C4 column was used for desalting and separation of α and β-chains. A manual and software-signal integration of charge states (M+17H to M+13H) was used.

Figure 1:
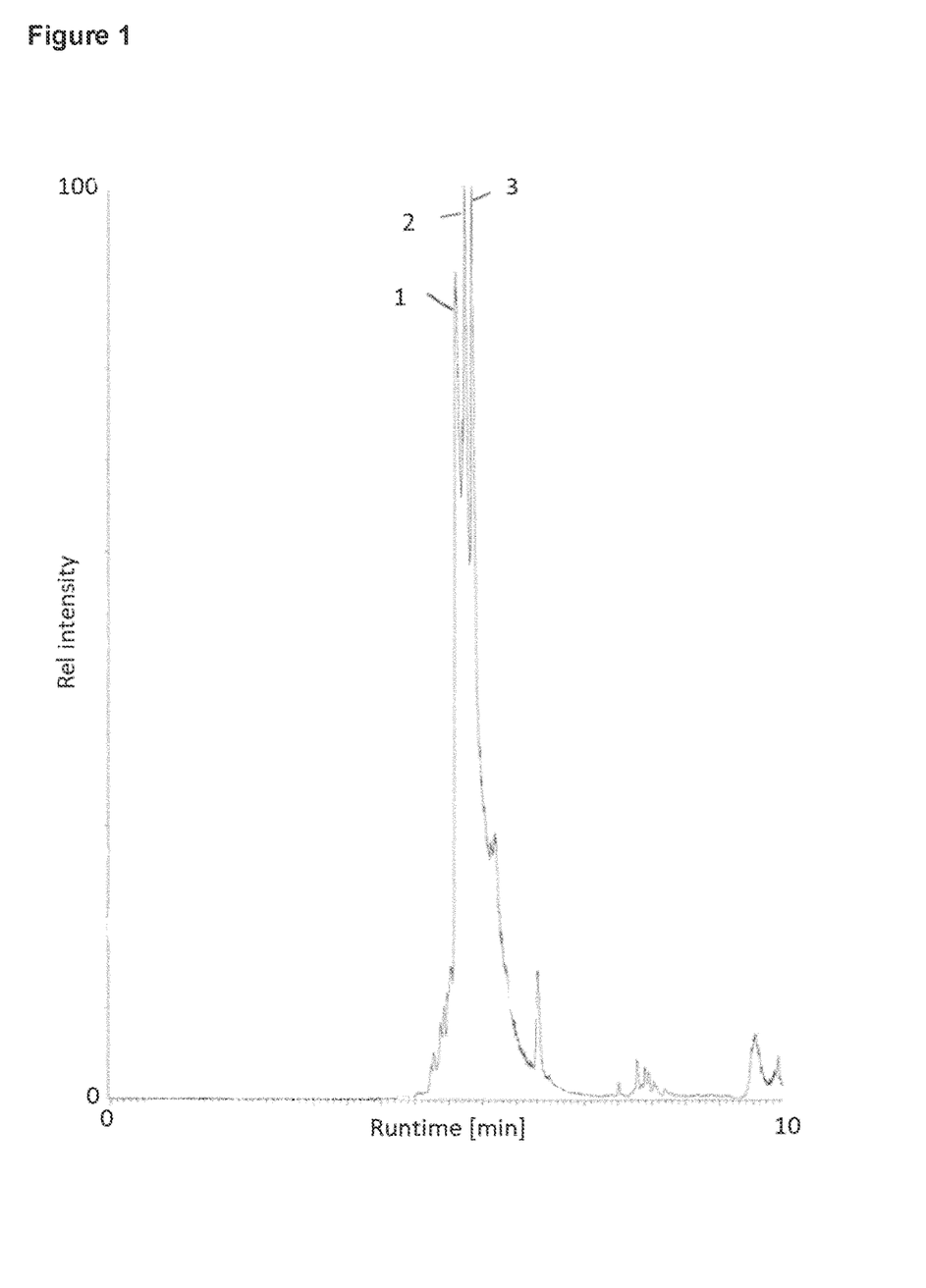
FIG. 1 depicts the LC-MS spectrum of a hemolysate without pre-enrichment (1: albumin; 2: HbA α-chain; 3: HbA β-chain).

In FIG. 1, the LC-MS spectrum of a hemolysate without pre-enrichment is shown (1: albumin; 2: HbA α-chain; 3: HbA β-chain).

Figure 2:
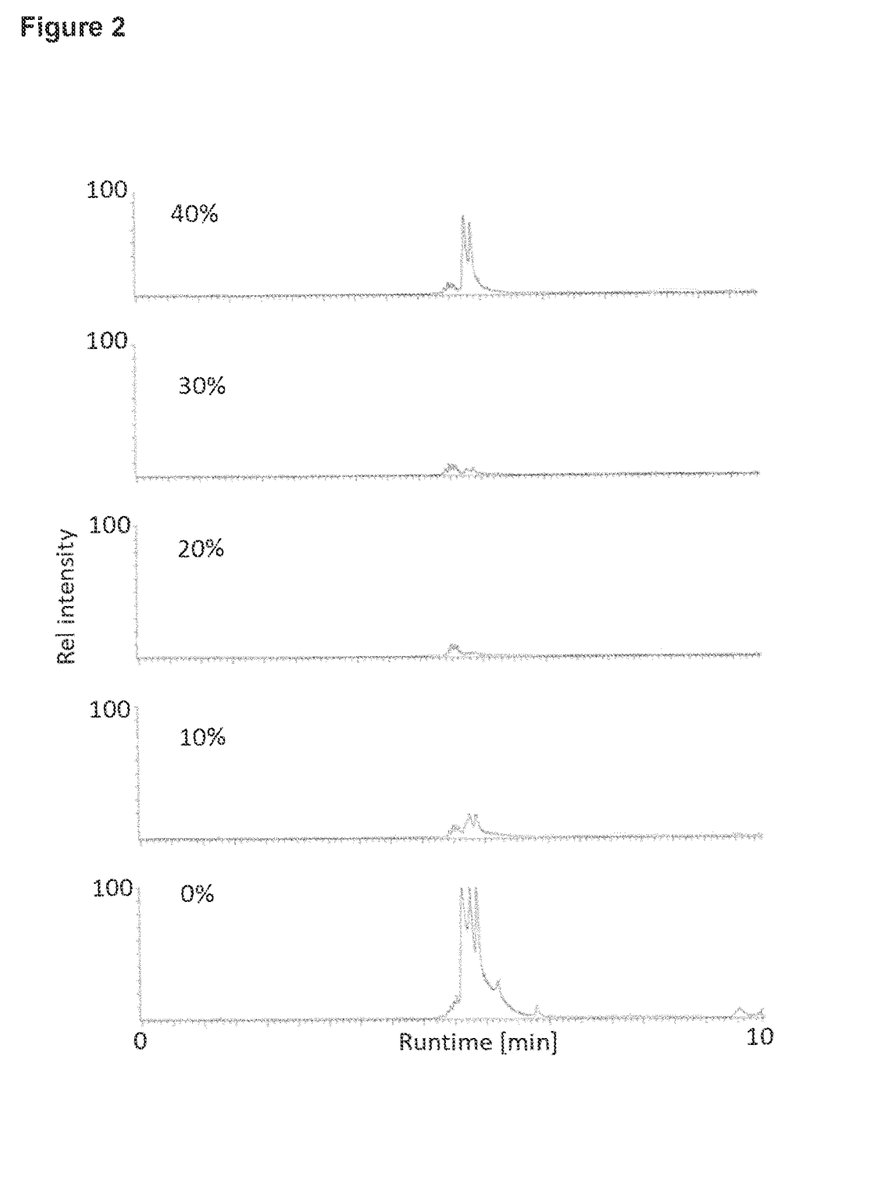
FIG. 2 depicts the LC-MS analysis of the 0% fraction, the 10% fraction, the 20% fraction, the 30% fraction and the 40% fraction from a batch of loaded beads (buffer pH 6).

FIG. 2 shows the LC-MS analysis of the 0% fraction, the 10% fraction, the 20% fraction, the 30% fraction and the 40% fraction from a batch of loaded beads (buffer pH 6) demonstrating separation of HbA chains from abundant albumin.

Figure 3:
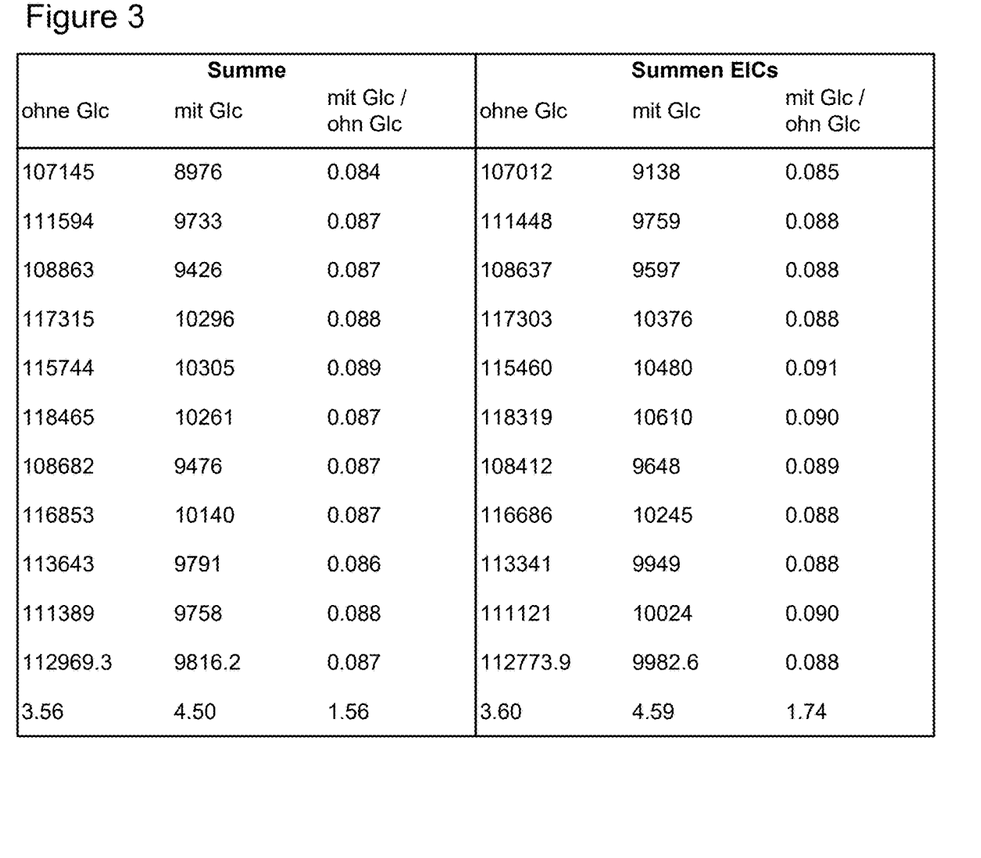
FIG. 3 depicts the results from a bead-based purification of whole blood hemolysates.

FIG. 3 shows the results from a bead-based purification of whole blood hemolysates demonstrating a coefficient of variation (CV) of HbA1c (w Glc)/HbA0 (w/o Glc) ratios of 1.56% and 1.74%, respectively, when testing 10 replicates of a sample by analyzing the different charge states of the proteins.

The invention claimed is:

1. A method for determining glycated hemoglobin A (HbA1c) in a sample, comprising:
 (a) providing a sample comprising hemoglobin A (HbA) molecules,
 (b) enriching intact hemoglobin A molecules in said sample, wherein hemoglobin A β-chain molecules are enriched versus hemoglobin A α-chain molecules, and
 (c) subjecting the sample comprising intact hemoglobin A molecules to an analysis by mass spectrometry (MS), wherein the amount or concentration of HbA1c molecules in the sample is determined.

2. The method of claim 1, wherein the sample in step (a) is a hemolysed whole-blood sample.

3. The method of claim 2, wherein enrichment step (b) comprises a first enrichment step (b)(i) comprising contacting the sample with a solid phase under conditions wherein the intact hemoglobin A molecules bind to the solid phase, and selectively eluting the bound intact hemoglobin A molecules from the solid phase.

4. The method of claim 3, wherein enrichment step (b) comprises a second enrichment step (b)(ii) comprising subjecting the hemolysed sample generated in step (a) or the enriched sample generated in enrichment step (b)(i) to a chromatographic enrichment step wherein intact hemoglobin A molecules are enriched.

5. The method of claim 4, wherein in enrichment step (b)(ii), intact hemoglobin A β-chain molecules are enriched versus hemoglobin A α-chain molecules by at least a factor of 10.

6. The method of claim 1, wherein step (c) comprises an analysis of intact hemoglobin A molecules, wherein the intact hemoglobin A molecules had not been subjected to digestion by a protease.

7. The method of claim 1, further comprising determining an amount or concentration of HbA0 molecules in the sample to determine a ratio of glycated hemoglobin A (HbA1c) to non-glycated hemoglobin A (HbA0).

8. The method of claim 7, wherein the ratio is determined with a coefficient of variation (CV) of 2.5% or less.

9. A kit comprising:
(i) enrichment means configured to enrich intact glycated HbA1c molecules comprising a solid phase having a hydrophobic surface configured to selectively bind the intact glycated HbA1c molecules, wherein hemoglobin A β-chain molecules are enriched versus hemoglobin A α-chain molecules,
(ii) a substantially neutral solid phase binding medium configured to dilute a hemolysed whole blood sample and bind the intact glycated HbA1c molecules to the solid phase (i) and
(iii) an elution medium comprising an organic water-miscible solvent configured to elute the bound intact glycated HbA1c molecules from the enrichment means (i).

10. A diagnostic system for determining glycated hemoglobin A (HbA1c) in a sample comprising
(i) at least one station for the preparation of samples comprising intact HbA1c molecules, wherein the preparation comprises hemolysis of a whole blood sample,
(ii) at least one enrichment station configured to selectively enrich the intact hemoglobin A molecules from the sample, wherein hemoglobin A β-chain molecules are enriched versus hemoglobin A α-chain molecules using the enrichment station, and
(iii) at least one station configured to analyze the intact hemoglobin A molecules by mass-spectrometry (MS) and to determine the amount or concentration of the intact HbA1c molecules in the sample.

11. The method of claim 1, wherein the intact hemoglobin A is the α- and/or the β-chain of hemoglobin A.

12. The method of claim 4, wherein in enrichment step (b)(ii) intact hemoglobin A β-chain molecules are enriched versus albumin molecules by at least a factor of 10.

13. The method of claim 6, wherein the protease is selected from the group consisting of trypsin and Glu-C.

14. The method of claim 11, wherein step (c) comprises an analysis of the α- and/or the β-chain of hemoglobin A, wherein the α- and/or the β-chain of hemoglobin A, have not been subjected to digestion by a protease.

15. The method of claim 14, wherein the protease is selected from the group consisting of trypsin and Glu-C.

16. The method of claim 1 further comprising determining an amount or concentration of HbA molecules in the sample to determine a ratio of glycated hemoglobin A (HbA1c) to total hemoglobin A (HbA).

* * * * *